US012521111B2

(12) United States Patent
Johnson et al.

(10) Patent No.: US 12,521,111 B2
(45) Date of Patent: Jan. 13, 2026

(54) SUTURING DEVICE

(71) Applicant: Durastat LLC, Austin, TX (US)

(72) Inventors: Jens Johnson, Austin, TX (US); Adam Azzara, Austin, TX (US); Kevin T. Foley, Memphis, TN (US)

(73) Assignee: DURASTAT LLC, Austin, TX (US)

( * ) Notice: Subject to any disclaimer, the term of this patent is extended or adjusted under 35 U.S.C. 154(b) by 86 days.

(21) Appl. No.: 18/665,665

(22) Filed: May 16, 2024

(65) Prior Publication Data

US 2025/0352199 A1 Nov. 20, 2025

(51) Int. Cl.

| | |
|---|---|
| ***A61B 17/04*** | (2006.01) |
| ***A61B 17/06*** | (2006.01) |
| *A61B 17/00* | (2006.01) |

(52) U.S. Cl.

CPC .................... *A61B 17/0469* (2013.01); *A61B 2017/00367* (2013.01); *A61B 2017/0608* (2013.01)

(58) Field of Classification Search

CPC ...... A61B 17/0469; A61B 2017/00367; A61B 2017/0608; A61B 5/1519; A61B 5/15194; A61B 5/15186; A61B 5/15144

See application file for complete search history.

(56) References Cited

U.S. PATENT DOCUMENTS

| | | | | |
|---|---|---|---|---|
| 5,665,096 A | | 9/1997 | Yoon | |
| 6,042,601 A | | 3/2000 | Smith | |
| 10,610,215 B2 | | 4/2020 | Anderson et al. | |
| 10,709,443 B2 | | 7/2020 | Anderson et al. | |
| 10,918,379 B2 | | 2/2021 | Kurd et al. | |
| 2006/0247671 A1 | * | 11/2006 | LeVaughn ........ | A61B 5/150717 600/583 |
| 2009/0125048 A1 | * | 5/2009 | Robbins ........... | A61B 5/150267 29/428 |
| 2010/0087754 A1 | * | 4/2010 | Rush ................ | A61B 5/150862 600/583 |
| 2011/0098736 A1 | | 4/2011 | Schraga | |
| 2012/0016385 A1 | | 1/2012 | Keren et al. | |

(Continued)

OTHER PUBLICATIONS

International Search Report filed in PCT/US2025/028076 mailed Jul. 3, 2025.

(Continued)

*Primary Examiner* — Anh T Dang
(74) *Attorney, Agent, or Firm* — RANKIN, HILL & CLARK LLP

(57) ABSTRACT

A suturing device includes a cannula, a needle pusher, a shuttle, a primer, a spring, and a button. The cannula includes a needle compartment defining a needle passage terminating in a distal opening. The needle pusher is provided in the cannula. The shuttle connects with the needle pusher. Movement of the shuttle results in movement of the needle pusher. The spring is positioned between and connected with the primer and the shuttle. Movement of the primer from an extended position toward a depressed position compresses the spring to exert a biasing force on the shuttle in an advance direction. Movement of the primer from the depressed position toward the extended position results in the spring pulling the shuttle in a retract direction. The spring biases the shuttle in the advance direction after the button is depressed, which pushes the needle pusher in the advance direction.

13 Claims, 5 Drawing Sheets

(56) References Cited

U.S. PATENT DOCUMENTS

| | | | |
|---|---|---|---|
| 2012/0283755 | A1 | 11/2012 | Gellman et al. |
| 2019/0008506 | A1 | 1/2019 | Kurd et al. |
| 2019/0015094 | A1 | 1/2019 | Anderson et al. |
| 2019/0021722 | A1 | 1/2019 | Anderson et al. |
| 2020/0375588 | A1 | 12/2020 | Veenhof et al. |

OTHER PUBLICATIONS

Office Action issued Apr. 9, 2025 in U.S. Appl. No. 18/150,875, 21 pages.

* cited by examiner

SUTURING DEVICE

BACKGROUND

The present disclosure relates generally to surgery and the placement of sutures, and more particularly to devices and methods for suture repair of the tissue.

Surgical closure using sutures is one approach to tissue repair. Oftentimes a needle driver or similar device is used to locate and to pass a suture needle through the tissue to be repaired. The suture needle attaches at one end to a predetermined length of suture, which can be stored in a suture package. Other wound closure devices, such as staples, and other repair devices, like mesh or patch reinforcements, are frequently used for repair.

Locating the tissue repair devices, especially when working in areas where it is difficult for a surgeon to access such as when working through a tubular retractor or other portal, can be very challenging. U.S. Pat. No. 10,610,215 B2 discloses a suturing device that includes an elongate body, a needle holder, and an actuator. The needle holder defines a needle passage that holds a needle. The actuator is configured such that movement from a first operating position toward a second operating position moves the needle in an advance direction. The actuator includes a button and a spring biasing the actuator toward the second operating position. The button is operatively connected with the spring so as to preclude the spring from moving the actuator toward the second operating position until after the button has been moved from a non-actuated position toward an actuated position. The suturing device disclosed in U.S. Pat. No. 10,610,215 B2 is particularly well suited for delivering one needle; however, reloading the device with another needle or the same needle that had been deployed can be problematic.

SUMMARY

In view of the foregoing, a suturing device includes a cannula, a needle pusher, a shuttle, a primer, a spring, and a button. The cannula includes a needle compartment defining a needle passage terminating in a distal opening. The needle pusher is provided in the cannula. The shuttle is connected with the needle pusher such that movement of the shuttle results in movement of the needle pusher. The primer is movable between an extended position and a depressed position. The spring is positioned between and connected with the primer and the shuttle. Movement of the primer from the extended position toward the depressed position compresses the spring to exert a biasing force on the shuttle in an advance direction when the primer is in the depressed position. Movement of the primer from the depressed position toward the extended position results in the spring pulling the shuttle in a retract direction. The button is operably engaged with the shuttle, where the spring biases the shuttle in the advance direction after the button is depressed, which pushes the needle pusher in the advance direction.

DETAILED DESCRIPTION

Figure 1:
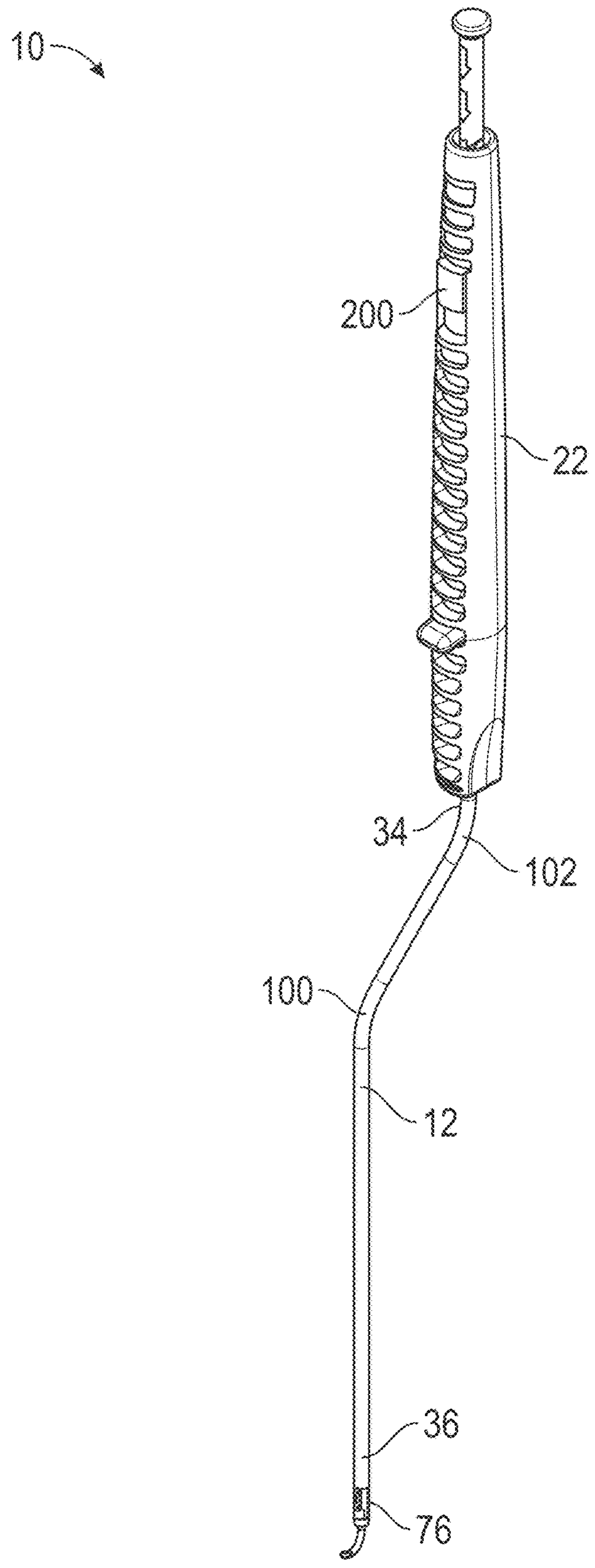
FIG. 1 is a perspective view of a suturing device.
Figure 2:
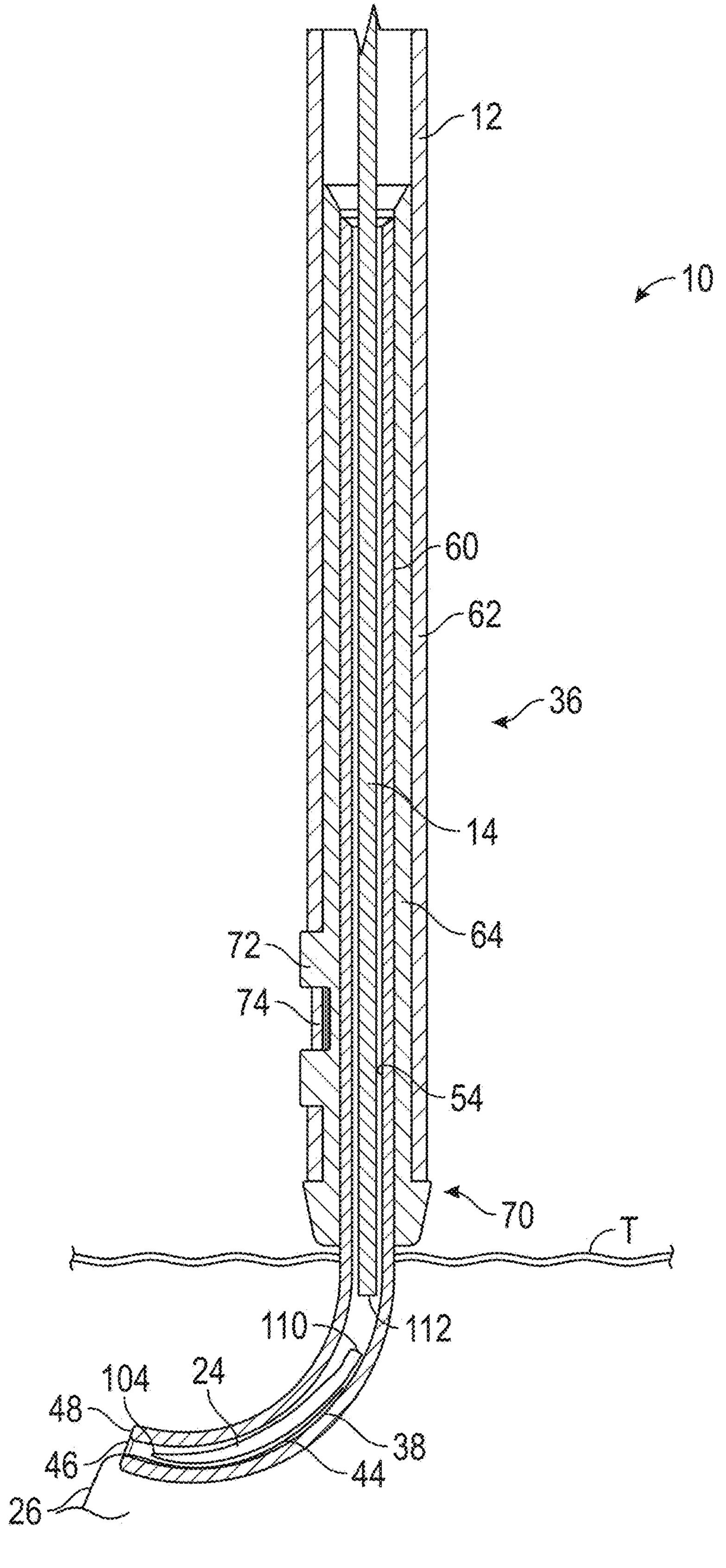
FIG. 2 is a cross-sectional view of the lower portion of the suturing device depicted in FIG. 1 positioned to repair a tissue tear.
Figure 3:
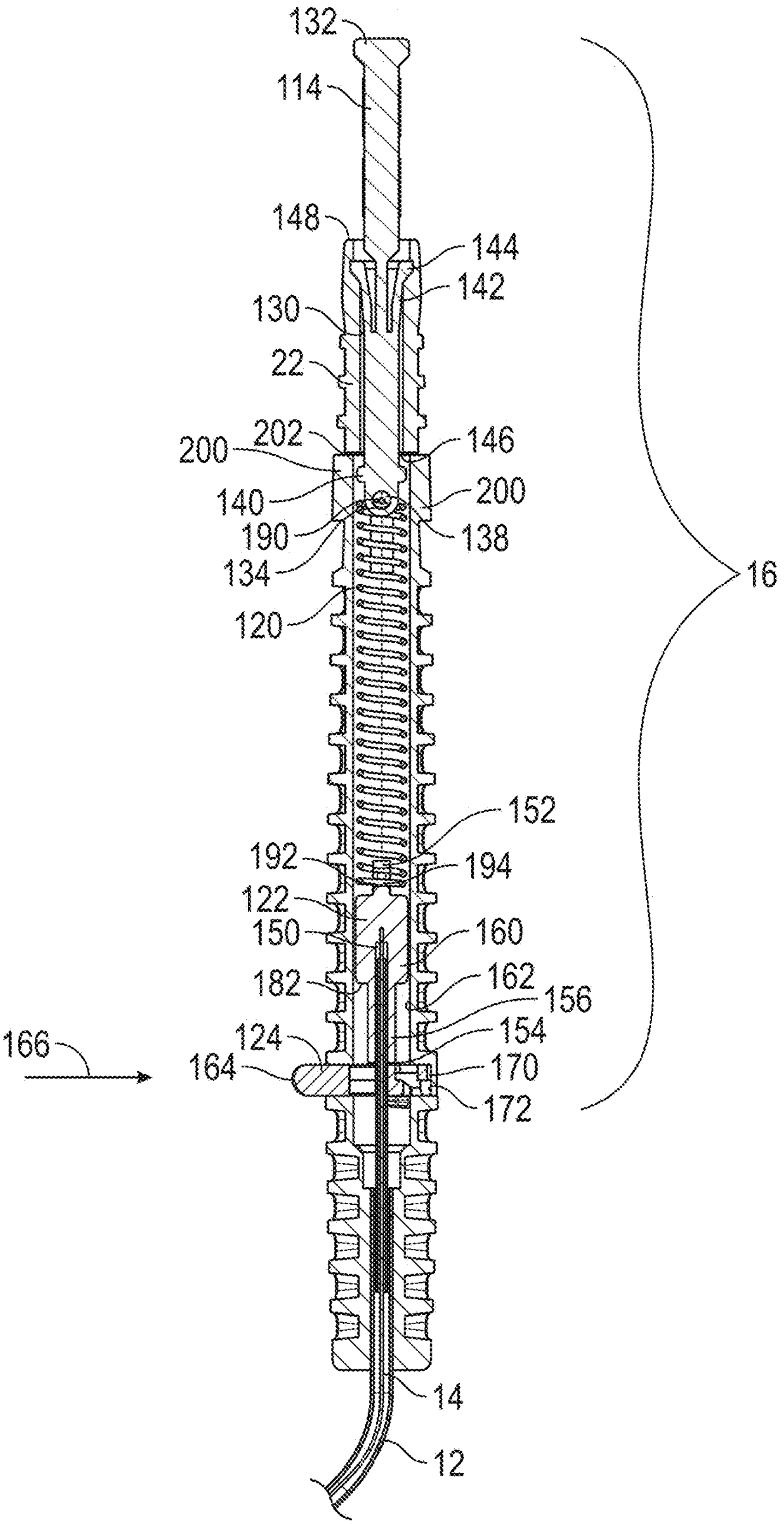
FIG. 3 is a cross-sectional view of a proximal portion of the suturing device depicted in FIG. 1 with a primer in an extended position.
Figure 4:
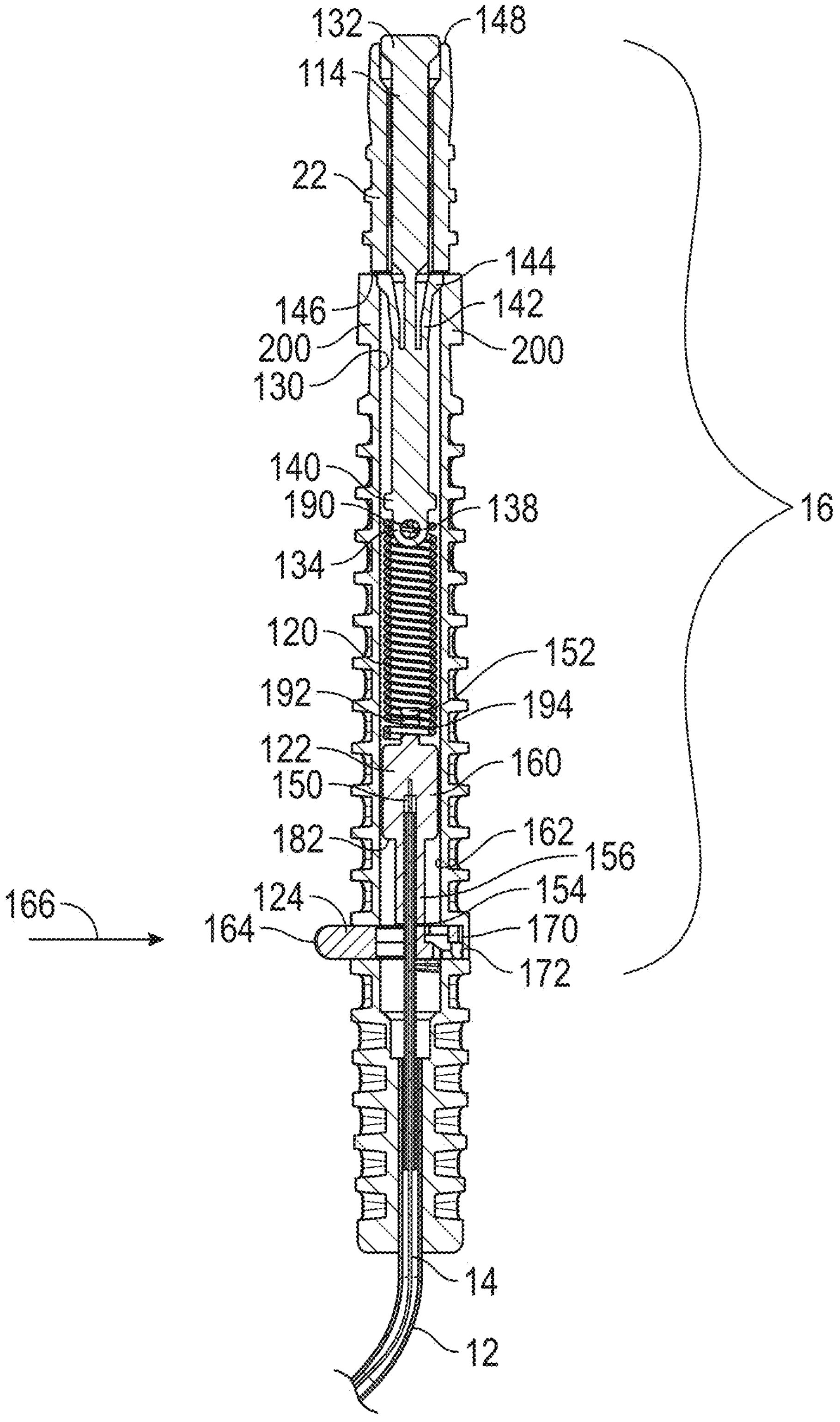
FIG. 4 is a cross-sectional view of a proximal portion of the suturing device depicted in FIG. 1 with a primer in a depressed position.

FIGS. 1-4 depict a suturing device 10 including a cannula 12 (FIG. 1), a needle pusher 14 (FIGS. 2, 3 and 4) and an actuator mechanism 16 (FIGS. 3 and 4). With reference to FIG. 1, the suturing device 10 can further include a handle 22 connected with the cannula 12. With reference to FIG. 2, the suturing device 10 can further include a needle 24 and a suture 26 connected with the needle 24. While, as depicted, the needle 24 is curved, the needle 24 can take different configurations, e.g., straight, without departing from the scope of the present application. The suturing device 10 is useful to repair tissue tears. The suturing device 10 can be particularly useful during a minimally invasive surgical procedure that is performed through a tubular retractor or other small surgical portal to accurately locate the needle 24 and the suture 26 to facilitate passing the needle 24 through target tissue T to be sutured; however the suturing device 10 is useful in other suturing procedures.

With reference to FIG. 1, the cannula 12 includes a proximal portion 34 and a distal portion 36. The proximal portion 34 is located nearer to and/or can be partially received in the handle 22. In FIG. 2, the distal portion 36 includes a needle compartment 38 that defines a needle passage 44 terminating in a distal opening 46. A distal edge surface 48 of the needle compartment 38 defines the distal opening 46. More particular to the embodiment disclosed in FIG. 2, the needle compartment 38 defines the needle passage 44, which is curved and extends along a curved needle passage axis. This aids in accommodating the needle 24, which can also be curved, in the needle passage 44. As illustrated, the needle compartment 38 has an arc length less 180 degrees, although the arc length could be longer.

As illustrated in FIG. 2, the cannula 12 includes an inner cannula 60 received in an outer cannula 62. Nevertheless, it is contemplated that the cannula 12 can be made from a single tube or more than two tubes connected with one another. As depicted, the inner cannula 60 is held in the outer cannula 62 by an insert 64. The inner cannula 60 and the insert 64 together form a distal end assembly 70 removably engaged with the outer cannula 62. In this regard, the insert 64 includes a protrusion 72 receivable in a notch 74 provided in an upside-down L-shaped slot 76 provided at a distal end of the outer cannula 62 when the inner cannula 60 and the insert 64 are inserted into the outer cannula 62. The distal portion 36, however, can take different configurations. In this regard, further embodiments of the distal portion 36 similar to the embodiment shown in FIGS. 1 and 2 are illustrated in U.S. patent application Ser. No. 18/150,875 and in U.S. patent application Ser. No. 18/150,868, which are each incorporated herein by reference.

In the depicted embodiments, the cannula 12 is circular in a cross section taken normal to the longest dimension of the cannula 12, however, the cannula 12 could take alternative configurations, such as polygonal or U-shaped. The cannula 12 has a bayonet configuration in the illustrated embodiment; however, the cannula 12 could take alternative configurations, such as straight along a longitudinal axis. As illustrated in FIG. 1, the cannula 12 includes a more distal bend 100 and a more proximal bend 102 to form the bayonet configuration.

With reference to FIGS. 3 and 4, the needle pusher 14 is operably connected with the actuator mechanism 16. The needle pusher 14 can be a wire, which can be made from nitinol. The needle pusher 14 is received in the cannula 12. More particularly, the needle pusher 14 is received in a needle pusher passage 54 located within the cannula 12. Upon actuation of the actuator mechanism 16, which will be described in more detail below, the needle pusher 14 is configured to push the needle 24 in an advance direction through the distal opening 46. With reference to FIG. 2, the needle 24 includes a first end 104, which is pointed, and a second end 110 that is opposite the first end 104. The suture 26 connects with the second end 110 of the needle 24. In the illustrated embodiment, at least a portion of the suture 26 extends through the distal opening 46 when the needle 24 is received in the needle compartment 38 prior to the actuator mechanism 16 being actuated.

Prior to actuation of the actuator mechanism 16, a distal end 112 of the needle pusher 14 is offset from the second end 110 of the needle 24. Although not shown in FIG. 2, prior to actuation of the actuator mechanism 16 a portion of the needle pusher 14 may extend into the needle passage 44. The needle pusher passage 54 also extends through the more distal bend 100 and the more proximal bend 102 in the cannula 12, depicted in FIG. 1, located in the proximal portion 34 of the cannula 12.

With reference to FIGS. 3 and 4, the actuator mechanism 16 is operably connected with the needle pusher 14. The actuator mechanism 16 includes a primer 114, a spring 120, a shuttle 122, and a button 124. The primer 114 is movable between an extended position shown in FIG. 3 and a depressed position shown in FIG. 4. The spring 120, which can be a coil spring, is positioned between and connected with the primer 114 and the shuttle 122. When the button 124 is not depressed, movement of the primer 114 from the extended position toward the depressed position compresses the spring 120 against the shuttle 122. The spring 120 exerts a biasing force on the shuttle 122 in the advance direction when the primer 114 is in the depressed position. The button 124 is operably engaged with the shuttle 122. The spring 120 biases the shuttle 122 in the advance direction after the button 124 is depressed, which moves the needle pusher 14 and pushes the needle 24 in the advance direction through the distal opening 46. The spring 120 can have an elastic limit corresponding to a spring deflection range that is at least as long as a range of motion of the primer 114 between the depressed position and the extended position. A first portion of the spring deflection range can correspond with the spring 120 being in a compressed state, where the primer 114 is in the depressed position. A second portion of the spring deflection range can corresponds with the spring 120 being in a tensioned state, where the primer 114 is moving from the depressed position toward the extended position.

The primer 114 is received in an upper bore 130 provided in the handle 22. The primer 114 includes a proximal head 132 and a distal end portion 134. A primer eyelet 138 is provided in the distal end portion 134 and a radial shoulder 140 is offset from the primer eyelet 138 toward the proximal head 132. The distal end portion 134, the primer eyelet 138 and the radial shoulder 140 operate as a locating feature for the spring 120, which will be described in more detail below.

The primer 114 further includes a resilient finger 142 (two resilient fingers are shown in FIGS. 3 and 4). A barb 144 is provided at a distal end of each resilient finger 142. As mentioned above, the primer 114 is movable between the extended position shown in FIG. 3, and the depressed position shown in FIG. 4 where the proximal head 132 is brought closer to and can come in contact with a proximal end 148 of the handle 22. A thumb of the operator of the suturing device 10 can be used to depress the primer 114, moving the primer 114 from the extended position toward the depressed position. A shoulder 146 can be provided in the handle 22 and the radial shoulder 140 can contact the shoulder 146 in the handle 22 when the primer 114 is in the extended position. As the primer 114 is depressed, the resilient fingers 142 compress while traveling through the upper bore 130 until passing the shoulder 146 in the handle 22 in the depressed position. When in the depressed position, the resilient finger 142, and more particularly the barb 144 on the resilient finger 142, selectively engages the shoulder 146 in the handle 22 to maintain the primer 114 in the depressed position.

The shuttle 122 includes a bore 150, which receives the needle pusher 14 to connect the needle pusher 14 with the shuttle 122. The needle pusher 14 is fixed to the shuttle 122 such that movement of the shuttle 122 results in movement of the needle pusher 14. The shuttle 122 includes a proximal end portion 152 that provides a locating feature for the spring 120. The shuttle 122 also includes a button contact surface 154, which is a distal end surface of the shuttle 122 as illustrated in FIGS. 3 and 4. The shuttle 122 also includes a reduced cross-sectional portion 156 extending from a relatively larger cross-sectional portion 160. The relatively larger cross-sectional portion 160 has a diameter slightly smaller than an inner diameter of an actuator cavity 162 provided in the handle to allow for translational movement of the shuttle 122 within the actuator cavity 162.

The button 124 includes an operator contact surface 164 and operates as a push button in the illustrated embodiment whereby an operator, such as a surgeon, depresses the button 124 in the direction of arrow 166 moving the button 124 from the undepressed position toward the actuated position. The button 124 also includes a finger 170 (see also FIG. 5) which contacts an inner side surface 172 provided in the handle 22 to bias the button 124 toward the undepressed position. As the operator depresses the button 124 in the direction of arrow 166, the finger 170 bends and operates similar to a spring.

Figure 5:
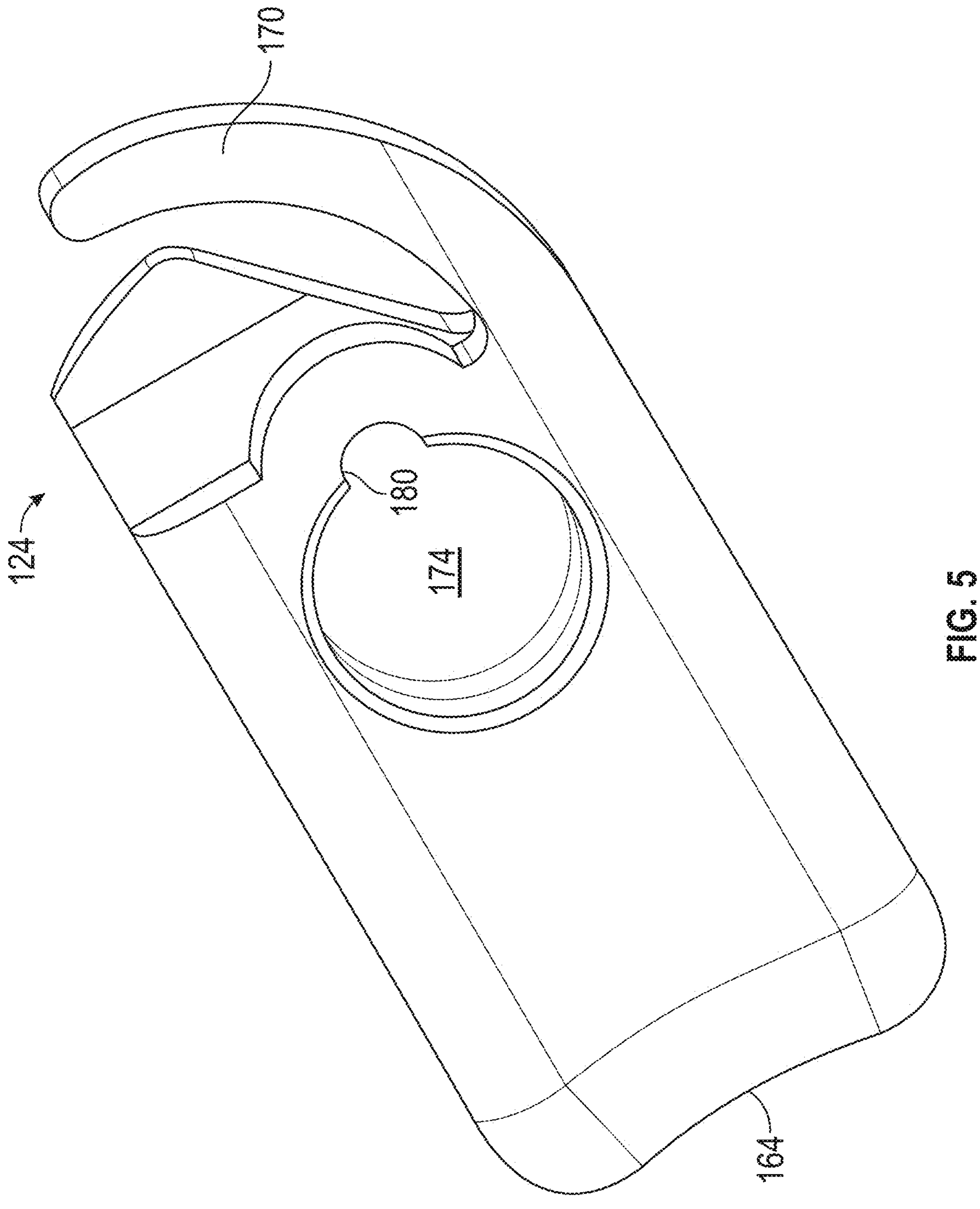
FIG. 5 is a perspective view of a button of the suturing device of FIG. 1.

As more clearly seen in FIG. 5, the button 124 includes an opening made up of a main portion 174 and a smaller portion 180. The main portion 174 of the opening is configured to receive the reduced cross-sectional portion 156 of the shuttle 122 when the main portion 174 of the opening is aligned with the reduced cross-sectional portion 156. This occurs when the operator presses the operator contact surface 164 in the direction of arrow 166 thus moving the button 124 to the right per the orientation shown in FIG. 3. The main portion 174 of the opening, however, is smaller than the relatively larger cross-sectional portion 160 of the shuttle 122. Accordingly, the travel distance of the shuttle 122 is limited by the distance between the button contact surface 154 and a transition surface 182 where the reduced cross-sectional portion 156 transitions to the relatively larger cross-sectional portion 160. With reference back to FIG. 5, the smaller portion 180 of the slider opening is configured to allow for passage of the needle pusher 14 to allow for the connection of the needle pusher 14 to the shuttle 122. When the button 124 is in the undepressed position (shown in FIGS. 1, 3 and 4), the button 124 contacts the shuttle 122 to preclude movement of the shuttle 122 with respect to the button 124. When an operator moves the button 124 in the direction of arrow 166, the button 124 is moved in the direction of arrow 166 which allows the main portion 174 of the slider opening to align with the reduced cross-sectional portion 156 of the shuttle 122, and the spring 120 moves the shuttle 122 downwardly (per the orientation shown in FIG. 4) such that the reduced cross-sectional portion 156 passes through the main portion 174 of the opening thus moving the needle pusher 14 and thus moving the needle 24 in the advance direction toward the distal opening 46.

With reference to FIGS. 3 and 4, the spring 120 is interposed between and connects the primer 114 with the shuttle 122. The primer 114 defines the primer eyelet 138, and the spring 120 includes a first end portion 190 which extends through the primer eyelet 138 such that the primer 114 is fixed with the first end portion 190. The shuttle 122 defines a shuttle eyelet 192. The spring 120 includes a second end portion 194 which extends through the shuttle eyelet 192 such that the shuttle 122 is fixed with the shuttle 122. In this manner, the spring 120 is fixed with each of the primer 114 and the shuttle 122 for exerting biasing forces on the shuttle 122 based on a position of the primer 114. The spring 120 is useful to pull the primer 114, and more particularly the reduced cross-sectional portion 156, back through the main portion 174 of the slider opening after the needle 24 has been deployed, which can be useful if re-loading of the suturing device 10 is desired. Movement of the primer 114 from the depressed position toward the extended position may tension the spring 120 to exert a biasing force on the shuttle 122 in a retract direction, opposite the advance direction.

When the primer 114 is in the depressed position, the spring 120 elastically compresses between the primer 114 and the shuttle 122 and exerts a force on the shuttle 122 capable of moving the shuttle 122 and the needle pusher 14 in the advance direction. Because of the manner the spring 120 connects with the primer 114 and the shuttle 122, movement of the primer 114 from the depressed position toward the extended position results in movement of the shuttle 122 and the needle pusher 14 in the retract direction. Because the finger 170 operates similar to a spring, the button 124 returns to a non-actuated position when the primer 114 is from the depressed position to the extended position.

The handle 22 connects with the cannula 12. The spring 120 and the shuttle 122 are positioned inside the handle 22. The primer 114 and the button 124 are at least partially received in the handle 22, where the button 124 is operably engaged with the shuttle 122, and the primer 114 is operatively engaged with the spring 120. As mentioned above, the primer 114 includes the resilient finger 142, and a portion of the resilient finger 142 selectively engages the shoulder 146 in the handle 22 to maintain the primer 114 in the depressed position as shown in FIG. 4. The handle 22 includes a release button 200 (two release buttons are shown in FIG. 4) aligned with the barb 144 when the barb 144 is engaged with the shoulder 146 when the primer 114 is in the depressed position. A cut out 202 is provided through the handle 22 from an exterior surface into the upper bore 130 to define an upper edge of each release button 200 in the illustrated embodiment, which allows each release button 200 to deflect inwardly. When the release button 200 is pressed by a user, the release button 200 is configured to deform inwards toward the barb 144 in the handle 22 to push the barb 144 away from contacting the shoulder 146 to allow the primer 114 to be pulled outwardly from the handle 22 toward the extended position from the depressed position. With the spring 120 connecting the primer 114 with the shuttle 122, movement of the primer 114 from the depressed position toward the extended position pulls the primer 114, and more particularly the reduced cross-sectional portion 156, back through the main portion 174 of the slider opening, which pulls the needle pusher 14 away from the distal opening 46. After the reduced cross-sectional portion 156 is pulled back through the main portion 174 of the slider opening, the finger 170 on the button 124 biases the button in a direction opposite to the arrow 166, which results in the button contact surface 154 on the shuttle 122 contacting the button 124 and the button 124 returning to an undepressed position, which is shown in FIGS. 3 and 4.

A suturing device has been described above with particularity. Modifications and alterations will occur to those upon reading and understanding the above detailed description. The invention, however, is not limited to only the embodiments described above. Instead, the invention is broadly defined by the appended claims and the equivalents thereof.

The invention claimed is:

1. A suturing device comprising:

a cannula including a needle compartment defining a needle passage terminating in a distal opening;

a needle pusher provided in the cannula;

a shuttle connected with the needle pusher such that movement of the shuttle results in movement of the needle pusher;

a primer movable between an extended position and a depressed position;

a spring positioned between and connected with the primer and the shuttle, wherein movement of the primer from the extended position toward the depressed position compresses the spring to exert a biasing force on the shuttle in an advance direction when the primer is in the depressed position, and movement of the primer from the depressed position toward the extended position moves the shuttle in a retract direction; and a button operably engaged with the shuttle, wherein the spring biases the shuttle in the advance direction after the button is depressed, which pushes the needle pusher in the advance direction, wherein the primer defines a primer eyelet, and the spring includes a first end portion which extends through the primer eyelet such that the primer is fixed with the first end portion, wherein when the primer is pushed from the extended position toward the depressed position, the primer compresses the spring toward the shuttle in the advance direction, and biases the needle pusher in the advance direction through the cannula, and when the primer is pulled from the depressed position toward the extended position, the primer tensions the spring away from the shuttle in the retract direction, and biases the needle pusher in the retract direction through the cannula.

2. The suturing device of claim 1, wherein the shuttle defines a shuttle eyelet, and the spring includes a second end portion which extends through the shuttle eyelet such that the shuttle is fixed with the second end portion.

3. The suturing device of claim 1, wherein the button is configured to return to an undepressed position after the spring pulls the shuttle through an opening in the button.

4. The suturing device of claim 3, further comprising a handle connected with the cannula, wherein the button includes a finger which contacts an inner side surface provided in the handle to bias the button toward the undepressed position.

5. The suturing device of claim 1, further comprising a handle connected with the cannula, wherein the spring and the shuttle are positioned inside the handle.

6. The suturing device of claim 5, wherein the primer includes a resilient finger for selectively engaging a shoulder in the handle when in the depressed position to maintain the primer in the depressed position.

7. The suturing device of claim 6, wherein the handle includes a release button aligned with a portion of the resilient finger that engages the shoulder when the primer is in the depressed position.

8. The suturing device of claim 7, wherein the resilient finger includes a barb that engages the shoulder when the primer is in the depressed position.

9. The suturing device of claim 7, wherein the handle includes a cut out provided through the handle to define an edge of the release button.

10. The suturing device of claim 1, further comprising a needle positioned in the needle passage, wherein the needle includes a first end, which is pointed, and a second end, and further comprising a suture connected with the second end of the needle, wherein at least a portion of the suture extends through the distal opening when the needle is received in the needle compartment prior to the button being actuated.

11. The suturing device of claim 1, wherein the cannula includes an inner cannula received in an outer cannula, the inner cannula including the needle compartment defining the needle passage terminating in the distal opening.

12. The suturing device of claim 11, further comprising a needle positioned in the needle passage, wherein the needle includes a first end, which is pointed, and a second end, and further comprising a suture connected with the second end of the needle, wherein at least a portion of the suture extends through the distal opening when the needle is received in the needle compartment prior to the button being actuated.

13. The suturing device of claim 12, further comprising an insert, wherein the inner cannula is held in the outer cannula by the insert, the inner cannula and the insert together form a distal end assembly that is removably engaged with the outer cannula.

* * * * *